(12) United States Patent
Nagano et al.

(10) Patent No.: US 11,277,905 B2
(45) Date of Patent: Mar. 15, 2022

(54) RADIATION IMAGING APPARATUS AND RADIATION IMAGING SYSTEM

(71) Applicant: CANON KABUSHIKI KAISHA, Tokyo (JP)

(72) Inventors: Kazumi Nagano, Tokyo (JP); Keiichi Nomura, Kawasaki (JP); Shinichi Takeda, Kawasaki (JP); Tomoyuki Oike, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 335 days.

(21) Appl. No.: 16/446,788

(22) Filed: Jun. 20, 2019

(65) Prior Publication Data

US 2019/0313525 A1 Oct. 10, 2019

Related U.S. Application Data

(63) Continuation of application No. PCT/JP2017/041949, filed on Nov. 22, 2017.

(30) Foreign Application Priority Data

Jan. 13, 2017 (JP) .............................. JP2017-004611

(51) Int. Cl.
*H05K 1/00* (2006.01)
*H05K 1/02* (2006.01)
*A61B 6/00* (2006.01)
*G01T 7/00* (2006.01)
(Continued)

(52) U.S. Cl.
CPC ............. *H05K 1/0271* (2013.01); *A61B 6/00* (2013.01); *A61B 6/42* (2013.01); *G01T 7/00* (2013.01); *H05K 1/0201* (2013.01); *H05K 1/144* (2013.01); *G01T 1/2006* (2013.01); *H05K 2201/10151* (2013.01)

(58) Field of Classification Search
CPC .... H05K 1/0271; H05K 1/0201; H05K 1/144; H05K 1/0203; H05K 1/0209; H05K 1/021; A61B 6/00; A61B 6/42; A61B 5/0093
See application file for complete search history.

(56) References Cited

U.S. PATENT DOCUMENTS

| 7,205,547 B2 | 4/2007 | Ishii et al. |
| 7,205,568 B2 | 4/2007 | Watanabe et al. |
| 7,256,404 B2 | 8/2007 | Inoue et al. |
| (Continued) | | |

FOREIGN PATENT DOCUMENTS

| JP | 2010-101805 | 5/2010 |
| JP | 2011-137804 | 7/2011 |
| (Continued) | | |

OTHER PUBLICATIONS

U.S. Appl. No. 16/520,760, Keiichi Nomura, filed Jul. 24, 2019.

*Primary Examiner* — Anthony M Haughton
(74) *Attorney, Agent, or Firm* — Venable LLP

(57) ABSTRACT

A radiation imaging apparatus comprises a sensor unit including two sensor boards stacked together, a base supporting the sensor unit, an electrical component on an opposite side to the sensor unit relative to the base, and a heat insulation member including a portion located between the electrical component and the sensor unit. A heat conductivity of the heat insulation member is lower than a heat conductivity of the base.

17 Claims, 5 Drawing Sheets

(51) Int. Cl.
*H05K 1/14* (2006.01)
*G01T 1/20* (2006.01)

(56) References Cited

U.S. PATENT DOCUMENTS

| | | | |
|---|---|---|---|
| 7,381,965 B2 | 6/2008 | Ishii et al. | |
| 7,391,029 B2 | 6/2008 | Takeda et al. | |
| 7,435,968 B2 | 10/2008 | Watanabe et al. | |
| 7,449,696 B2 * | 11/2008 | Joshi | G01T 1/2018 250/363.03 |
| 7,465,933 B2 | 12/2008 | Ishii et al. | |
| 7,488,948 B2 | 2/2009 | Ishii et al. | |
| 7,514,686 B2 | 4/2009 | Ogawa et al. | |
| 7,535,506 B2 | 5/2009 | Nomura et al. | |
| 7,538,330 B2 | 5/2009 | Nomura et al. | |
| 7,541,617 B2 | 6/2009 | Mochizuki et al. | |
| 7,557,355 B2 | 7/2009 | Mochizuki et al. | |
| 7,595,493 B2 | 9/2009 | Okada et al. | |
| 7,629,564 B2 | 12/2009 | Mochizuki et al. | |
| 7,687,790 B2 * | 3/2010 | Utschig | A61B 6/102 250/515.1 |
| 7,714,294 B2 | 5/2010 | Sawada et al. | |
| 7,723,693 B2 | 5/2010 | Okada et al. | |
| 7,750,422 B2 | 7/2010 | Watanabe et al. | |
| 7,777,167 B2 | 8/2010 | Takeda et al. | |
| 7,812,317 B2 | 10/2010 | Watanabe et al. | |
| 7,858,947 B2 | 12/2010 | Mochizuki et al. | |
| 7,893,405 B2 | 2/2011 | Nagano et al. | |
| 7,923,695 B2 | 4/2011 | Ishii et al. | |
| 7,952,058 B2 | 5/2011 | Nomura et al. | |
| 8,115,177 B2 | 2/2012 | Takeda et al. | |
| 8,154,641 B2 | 4/2012 | Nomura et al. | |
| 8,304,735 B2 | 11/2012 | Inoue et al. | |
| 8,440,975 B2 | 5/2013 | Inoue et al. | |
| 8,648,312 B2 | 2/2014 | Ichimura et al. | |
| 8,653,463 B2 | 2/2014 | Sawada et al. | |
| 8,653,465 B2 | 2/2014 | Nagano et al. | |
| 8,704,185 B2 | 4/2014 | Ishida et al. | |
| 8,748,836 B2 * | 6/2014 | Sato | A61B 6/44 250/370.09 |
| 9,006,665 B2 | 4/2015 | Nagano et al. | |
| 9,011,000 B2 * | 4/2015 | Tagawa | A61B 6/4283 378/189 |
| 9,054,012 B2 | 6/2015 | Nomura et al. | |
| 9,081,104 B2 | 7/2015 | Sawada et al. | |
| 9,110,176 B2 | 8/2015 | Oike et al. | |
| 9,161,730 B2 * | 10/2015 | Ham | A61B 6/4283 |
| 9,234,271 B2 | 1/2016 | Nomura et al. | |
| 9,354,333 B2 | 5/2016 | Inoue et al. | |
| 9,366,767 B2 | 6/2016 | Inoue et al. | |
| 9,568,614 B2 | 2/2017 | Ishida et al. | |
| 10,119,859 B2 * | 11/2018 | Suzuki | G01T 1/2018 |
| 10,197,684 B2 | 2/2019 | Terui et al. | |
| 10,283,555 B2 | 5/2019 | Ichimura et al. | |
| 10,317,540 B2 * | 6/2019 | Akamatsu | G01T 1/24 |
| 10,349,914 B2 | 7/2019 | Takenaka et al. | |
| 10,722,195 B2 * | 7/2020 | Suwa | A61B 6/4405 |
| 2010/0104067 A1 * | 4/2010 | Okada | G01T 1/00 378/62 |
| 2012/0219115 A1 | 8/2012 | Okada et al. | |
| 2013/0153775 A1 | 6/2013 | Nomura et al. | |
| 2013/0168559 A1 | 7/2013 | Saruta et al. | |
| 2013/0187054 A1 | 7/2013 | Ishii et al. | |
| 2013/0221198 A1 | 8/2013 | Sawada et al. | |
| 2013/0308755 A1 | 11/2013 | Ishida et al. | |
| 2014/0034836 A1 | 2/2014 | Takei et al. | |
| 2014/0226795 A1 * | 8/2014 | Kitano | A61B 6/4283 378/189 |
| 2014/0284485 A1 | 9/2014 | Nagano et al. | |
| 2015/0014546 A1 | 1/2015 | Ichimura et al. | |
| 2016/0161616 A1 * | 6/2016 | Nakayama | G01T 1/244 250/370.15 |
| 2016/0172414 A1 | 6/2016 | Saruta et al. | |
| 2016/0270755 A1 | 9/2016 | Takenaka et al. | |
| 2017/0285189 A1 | 10/2017 | Ryu et al. | |
| 2018/0070906 A1 | 3/2018 | Terui et al. | |
| 2019/0011574 A1 * | 1/2019 | Suwa | G01T 1/2018 |
| 2019/0029618 A1 | 1/2019 | Sato et al. | |
| 2019/0139666 A1 | 5/2019 | Sasaki et al. | |
| 2019/0313525 A1 * | 10/2019 | Nagano | H05K 1/0271 |

FOREIGN PATENT DOCUMENTS

| | | |
|---|---|---|
| JP | 2014-178308 | 9/2014 |
| JP | 2015-038435 | 2/2015 |
| JP | 2016-200543 | 12/2016 |

* cited by examiner

RADIATION IMAGING APPARATUS AND RADIATION IMAGING SYSTEM

CROSS-REFERENCE TO RELATED APPLICATIONS

This application is a Continuation of International Patent Application No. PCT/JP2017/041949, filed Nov. 22, 2017, which claims the benefit of Japanese Patent Application No. 2017-004611, filed Jan. 13, 2017, both of which are hereby incorporated by reference herein in their entirety.

BACKGROUND OF THE INVENTION

Field of the Invention

The present invention relates to a radiation imaging apparatus and a radiation imaging system.

Background Art

Patent Literature 1 describes a radiation imaging apparatus for obtaining a radiation image using radiation of a plurality of energies with a single radiation exposure (so-called one-shot method). This radiation imaging apparatus has two sensor boards stacked together. Low energy radiation is detected by the sensor board that is closer to the incident surface. On the other hand, high energy radiation is partially absorbed by the sensor board that is closer to the incident surface, and the remainder thereof is absorbed by the sensor board that is further from the incident surface. The two sensor boards are disposed on one surface of a support board. Electrical components such as integrated circuits that control the sensor boards and integrated circuits that process signals obtained by the sensor boards are disposed on the other surface of the support board.

CITATION LIST

Patent Literature

PTL1: Japanese Patent Laid-Open No. 2010-101805

With the radiation imaging apparatus of Patent Literature 1, the two sensor boards and the electrical components are housed in the same casing. Thus, these sensor boards are both affected by the heat produced by the electrical components, with the sensor board that is closer to the electrical components being more susceptible to the effects of the heat. Deterioration in the image quality obtained by the one-shot method can result when the two sensor boards are affected differently by the heat. One aspect of the present invention provides a technology for improving image quality stability by reducing the difference in how the two sensor boards stacked together are affected by electrical components within the same casing.

SUMMARY OF THE INVENTION

In view of the above problems, a radiation imaging apparatus is provided, the radiation imaging apparatus including a sensor unit including two sensor boards stacked together, a base supporting the sensor unit, an electrical component on an opposite side to the sensor unit relative to the base, and a heat insulation member including a portion located between the electrical component and the sensor unit, wherein a heat conductivity of the heat insulation member is lower than a heat conductivity of the base.

Further features of the present invention will become apparent from the following description of exemplary embodiments with reference to the attached drawings.

BRIEF DESCRIPTION OF THE DRAWINGS

The accompanying drawings, that are incorporated in and constitute a part of the specification, illustrate embodiments of the invention and, together with the description, serve to explain the principles of the invention.

DESCRIPTION OF THE EMBODIMENTS

Embodiments of the present invention will now be described with reference to the accompanying drawings. The same reference signs are given to similar elements throughout the various embodiments, and redundant description will be omitted. Also, the embodiments can be modified or combined as appropriate. Some embodiments of the present invention relate to a radiation imaging apparatus that is applied to medical imaging diagnostic apparatuses, nondestructive inspection apparatuses, analysis apparatuses and the like and detects radiation such as X-rays, alpha rays, beta rays and gamma rays, an example of which is a flat panel detector (FPD). The radiation imaging apparatus may be a portable radiation imaging apparatus for shooting images of patients who cannot be taken to an imaging room.

First Embodiment

Figure 1A:
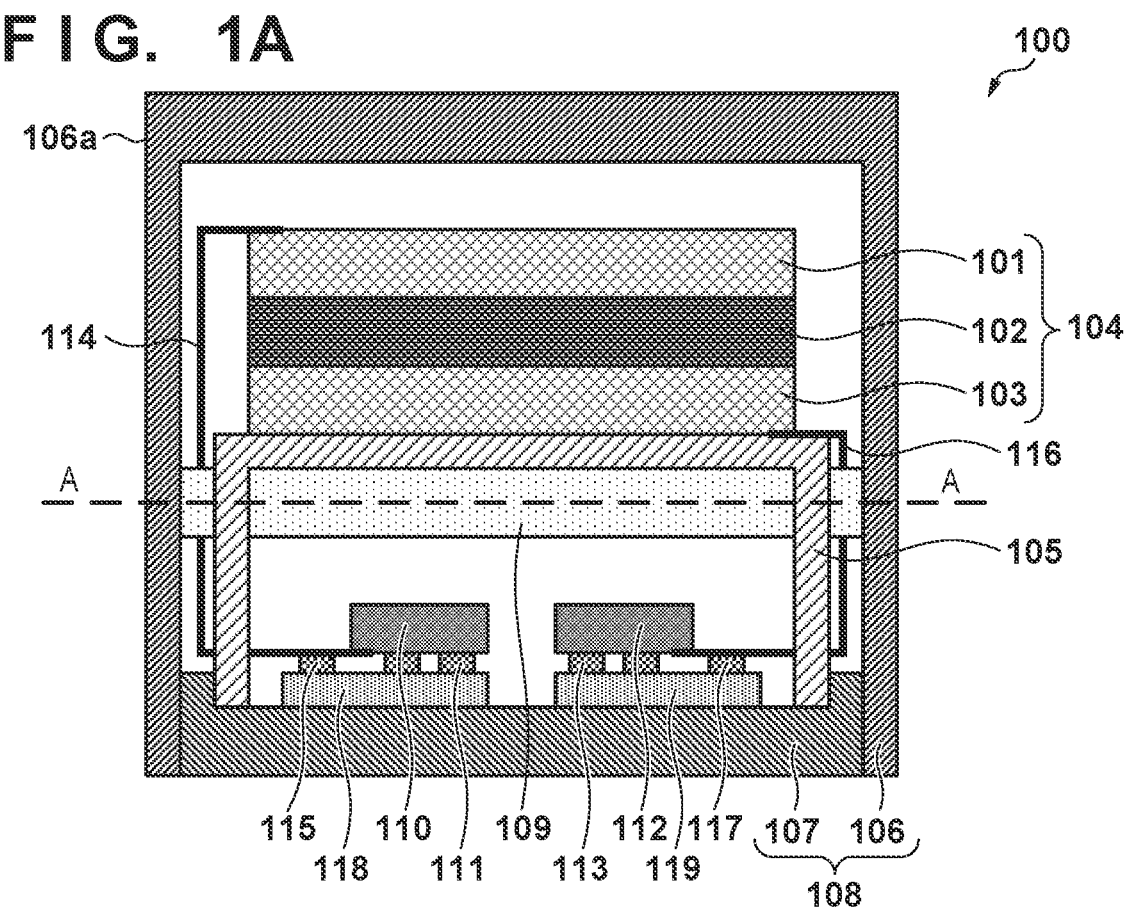
FIGS. 1A and 1B are diagrams illustrating an exemplary configuration of a radiation imaging apparatus of a first embodiment of the present invention.
Figure 1B:
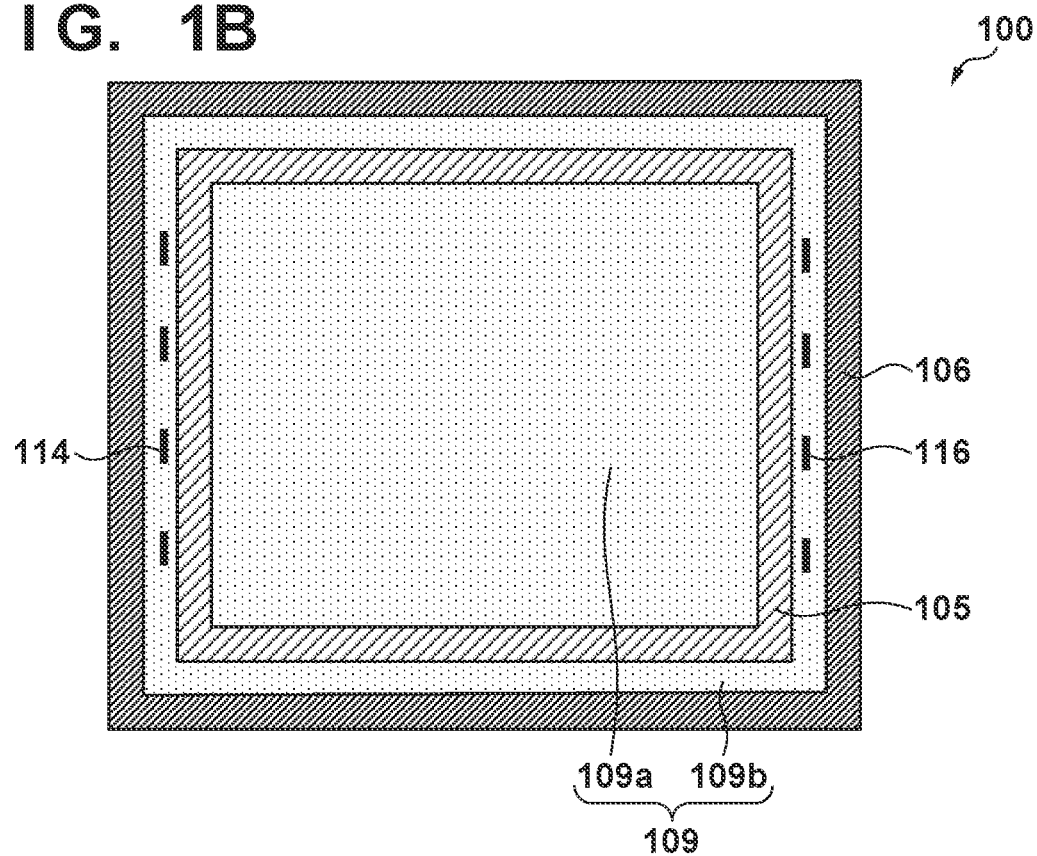

A radiation imaging apparatus 100 according to a first embodiment will be described, with reference to FIGS. 1A and 1B. FIG. 1A shows a cross-sectional view of the radiation imaging apparatus 100 in a plane orthogonal to an incident surface 106a. FIG. 1B shows a cross-sectional view of the radiation imaging apparatus 100 along an A-A line of FIG. 1A.

The radiation imaging apparatus 100 has the constituent elements shown in FIGS. 1A and 1B, notably, a sensor unit 104, a base 105, a heat insulation member 109, mount boards 110 and 112, and a casing 108. The casing 108 is constituted by an upper cover 106 and a lower cover 107. The upper cover 106 and the lower cover 107 each have a box-like shape constituted by a bottom plate and side walls connected to an outer periphery of this bottom plate. Space is formed inside the casing 108, by the lower cover 107 blocking the open side of the upper cover 106. The bottom plate of the upper cover 106 serves as the incident surface 106a of radiation. That is, the radiation imaging apparatus 100 is exposed to radiation from the upper side of FIG. 1A when the radiation imaging apparatus 100 is in use. The upper cover 106 is formed from a material with low absorption of radiation, such as plastic, carbon or CFRP (Carbon Fiber Reinforced Plastics), for example. On the other hand, the lower cover 107 may be formed from a material with high absorption of radiation.

The sensor unit 104 is housed in the casing 108. The sensor unit 104 has two sensor boards 101 and 103 and a filter 102. The sensor board 101 and the sensor board 103 are stacked together, and the filter 102 is located between these two sensor boards 101 and 103. Because the sensor board 101 and the sensor board 103 may have the same configuration, the sensor board 101 will be described below.

The sensor board 101 may be a so-called DR (Digital Radiography) sensor. The sensor board 101 has a plurality of pixels, and each pixel generates an electrical signal that depends on the amount of radiation that is incident. Because the configuration of the sensor board 101 may be an existing configuration, an example thereof will be briefly described below. Each pixel of the sensor board 101 is constituted by a switch element such as a thin film transistor (TFT), a photoelectric conversion unit made of amorphous silicon (a-Si) or the like and a scintillator layer being disposed on an insulated substrate such as a glass substrate. Radiation is converted into visible light by the scintillator layer, and the photoelectric conversion unit converts this visible light into electric charge. CsI, GOS ($Gd_2O_2S$:Tb) or the like are used as the scintillator layer. In particular, Tl (thallium) or Na (sodium) is used as an activator for CsI (cesium iodide). The scintillator layer is covered with a protective film such as poly-para-xylylene (parlene), a hot melt resin, or a hot melt resin and aluminum laminated sheet. Each pixel may have a conversion unit constituted by amorphous selenium (a-Se) or the like that converts radiation directly into electric charge, instead of having a scintillator layer.

The filter 102 reduces radiation of a predetermined wavelength band. For example, the filter 102 reduces radiation on the low energy side. A metal filter may be used as the filter 102. For example, a copper filter that reduces radiation of 33 keV or less may be used.

The low energy component of radiation that enters through the incident surface 106a of the casing 108 is converted into an electrical signal by the sensor board 101 that is closer to the incident surface. The remaining low energy component of radiation that passes through the sensor board 101 is absorbed by the filter 102. The high energy component of radiation that passes through the sensor board 101 is converted into an electrical signal by the sensor board 103 that is further from the incident surface. Energy subtraction radiography is performed, by taking the difference of images obtained by the two sensor boards 101 and 103. Because most of the low energy component of the radiation is absorbed by the sensor board 101, the filter 102 may be omitted.

The base 105 is housed in the casing 108. The base 105 has a box-like shape constituted by a support plate and side walls connected to an outer periphery of this support plate. An opening of the base 105 is provided on the opposite side (lower side of FIG. 1A) to the sensor unit 104. Alternatively, the base 105 may be constituted by a support plate and a plurality of legs connected to the support plate. The base 105 supports the sensor unit 104. For example, the sensor unit 104 is fixed to the back side (upper side of FIG. 1A) of the support plate of the base 105. Also, the base 105, specifically, the end portion of the side walls, is fixed to the lower cover 107 of the casing 108. The robustness of the radiation imaging apparatus 100 improves, as a result of the radiation imaging apparatus 100 having such a base 105. The base 105 is formed by resin or metal, for example.

The mount boards 110 and 112 are housed in the casing 108. The mount boards 110 and 112 are on the opposite side in the sensor unit 104 relative to the base 105. The mount board 110 is connected to the sensor board 101 via a cable 114 such as a FPC (flexible printed circuit board). The mount board 112 is connected to the sensor board 103 via a cable 116 such as a FPC. An electrical component 111 is installed on the mount board 110. The electrical component 111 includes an integrated circuit (e.g., drive circuit) that controls operations of the sensor board 101 and/or an integrated circuit (e.g., amplifier IC, readout circuit) that processes signals from the sensor board 101. An electrical component 115 such as an integrated circuit is installed on the cable 114. An electrical component 113 is installed on the mount board 112. The electrical component 113 include an integrated circuit (e.g., drive circuit) that controls operations of the sensor board 103 and/or an integrated circuit (e.g., amplifier IC, read-out circuit) that processes signals from the sensor board 103. An electrical component 117 such as an integrated circuit is installed on the cable 116. In order to suppress heat propagation to the surrounding area due to heat produced by the electrical components 115 and 117, the cables 114 and 116 may be provided with a heat insulation layer. The electrical components 111, 113, 115 and 117 are on the opposite side to the sensor unit 104 relative to the base 105. Hereinafter, the electrical components 111, 113, 115 and 117 will be referred to as the electrical component 111 and the like.

Heat dissipation members 118 and 119 are housed in the casing 108. The heat dissipation member 118 contacts both the electrical components 111 and 115 and the lower cover 107, and releases heat produced by the electrical components 111 and 115 to outside of the radiation imaging apparatus 100 through the lower cover 107. The heat dissipation member 119 contacts both the electrical components 113 and 117 and the lower cover 107, and releases heat produced by the electrical components 113 and 117 to outside of the radiation imaging apparatus 100 through the lower cover 107. The heat dissipation members 118 and 119 are constituted by a heat dissipation rubber, for example.

The heat insulation member 109 is housed in the casing 108. The heat insulation member 109 includes a portion located between the electrical component 111 and the like and the sensor unit 104. The heat insulation member 109 suppresses transfer of heat produced by the electrical component 111 and the like (particularly heat from the integrated circuits following an increase in power consumption) to the sensor unit 104. The heat conductivity of the heat insulation member 109 is lower than the heat conductivity of the base 105. For example, the heat conductivity of the heat insulation member 109 is 0.01 to 0.5 W/(m·K).

The heat insulation member 109 is, for example, solid resin, a laminated body, a filler structure formed by cured liquid resin, or foamed resin having a high insulation effect. A resin material, such as phenol resin, epoxy resin, silicone resin, acrylic resin, PEEK resin, PET (polyethylene terephthalate), VCM/PVC, polycarbonate, fluoro resin, urethane resin, rubber or the like, is given as an example of the material of the heat insulation member 109. The heat insulation member 109 may be liquid resin filling. The heat insulation member 109 may not include chlorine in consideration of corrosion. The heat insulation members 109 may be heat-cured resin or ultraviolet-cured resin.

The inside of the casing 108 is divided into a plurality of spaces by the heat insulation member 109, and the sensor unit 104 and the electrical component 111 and the like are located in different spaces to each other. In the first embodiment, the heat insulation member 109 includes an inner side portion 109a and an outer side portion 109b. The inner side portion 109a of the heat insulation member 109 is on the opposite side to the sensor unit 104 relative to the base 105. In planer view of the incident surface 106a, the inner side portion 109a may be comparable in size to the sensor unit 104, may be larger than the sensor unit 104, or may be smaller than the sensor unit 104. Direct heat transfer from the electrical component 111 and the like to the sensor unit 104 is suppressed by the inner side portion 109a of the heat insulation member 109. The outer side portion 109b of the heat insulation member 109 blocks the space between the upper cover 106 and the base 105. Specifically, the outer side portion 109b of the heat insulation member 109 contacts both the upper cover 106 and the base 105. Heat transfer due to convection from the electrical component 111 and the like to the sensor unit 104 is suppressed by the outer side portion 109b of the heat insulation member 109. Also, shock resistance from the side of the casing 108 improves, due to the outer side portion 109b of the heat insulation member 109.

Because heat transfer from the electrical component 111 and the like to the sensor unit 104 is suppressed by the heat insulation member 109, S/N degradation due to the difference in the temperature rise of the two sensor boards 101 and 103 within the sensor unit 104 is reduced. The image quality of images obtained by the radiation imaging apparatus 100 thereby improves.

Second Embodiment

Figure 2A:
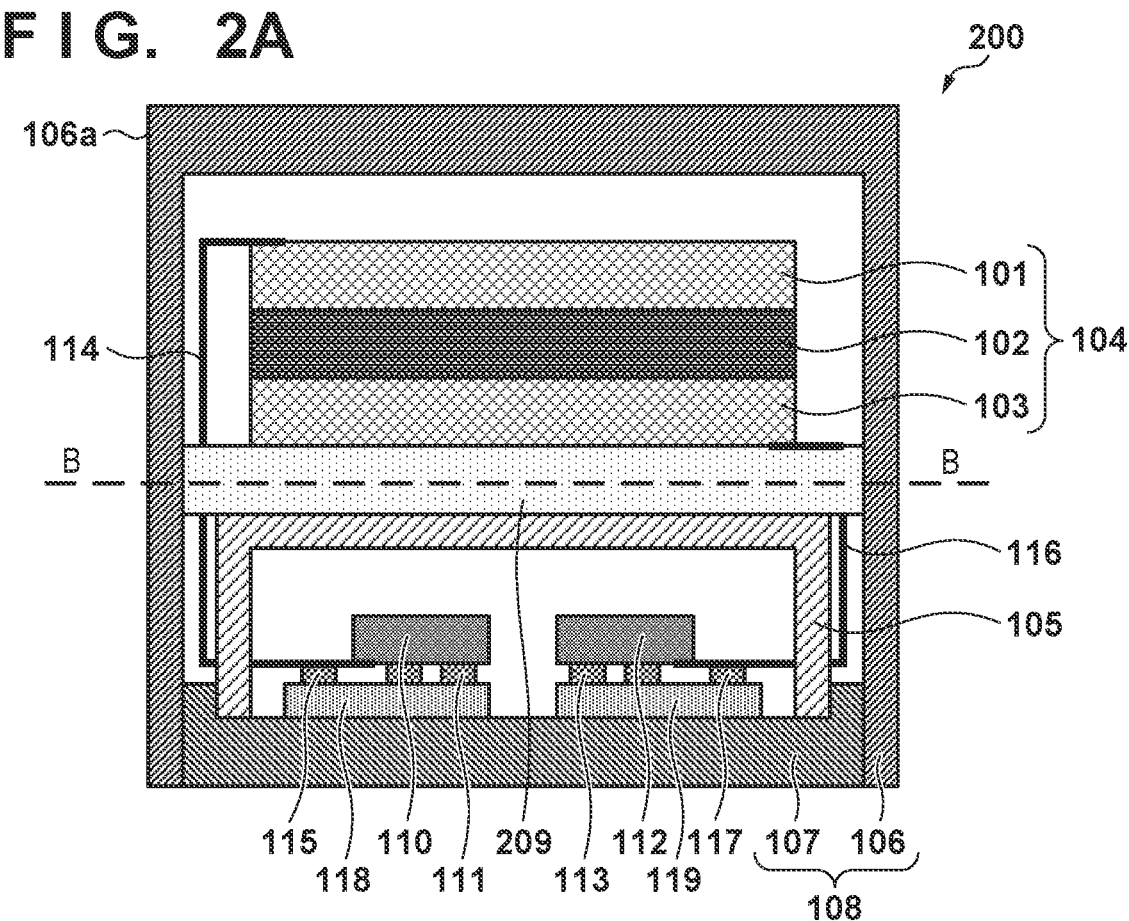
FIGS. 2A and 2B are diagrams illustrating an exemplary configuration of a radiation imaging apparatus of a second embodiment of the present invention.
Figure 2B:
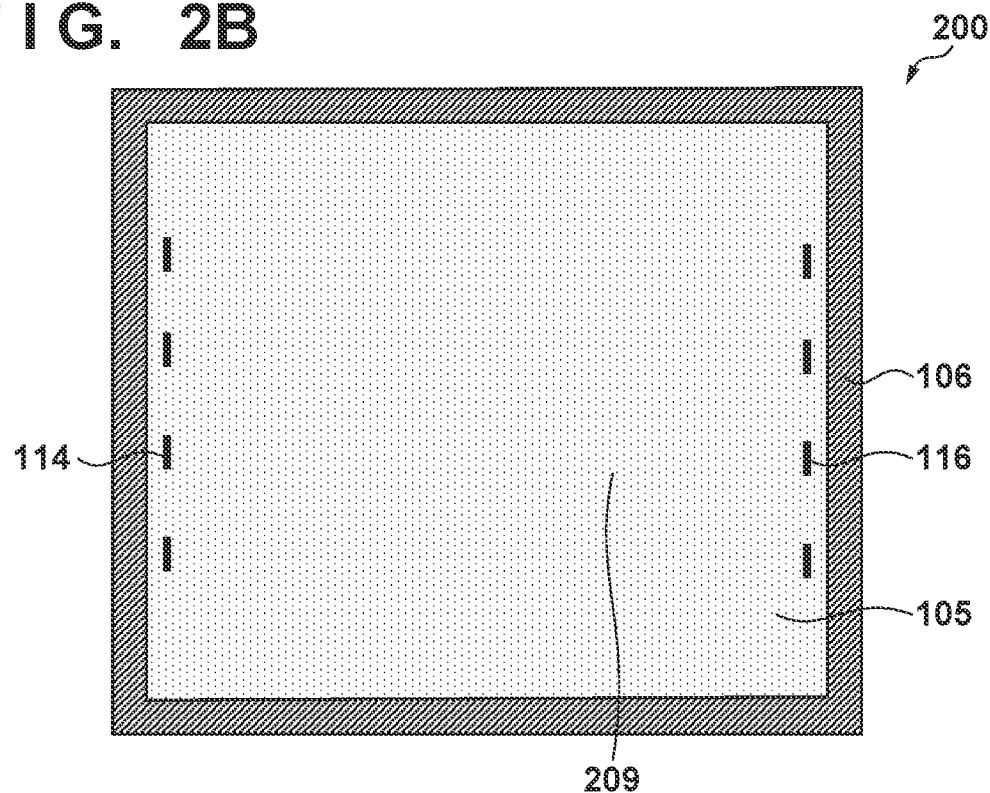

A radiation imaging apparatus 200 according to the second embodiment will be described, with reference to FIGS. 2A and 2B. FIG. 2A shows a cross-sectional view of the radiation imaging apparatus 200 in a plane orthogonal to the incident surface 106a. FIG. 2B shows a cross-sectional view of the radiation imaging apparatus 200 along a B-B line of FIG. 2A. The radiation imaging apparatus 200 differs from the radiation imaging apparatus 100 in terms of having a heat insulation member 209 instead of the heat insulation member 109, and may otherwise be the same. Thus, in the second embodiment, similar description to the first embodiment will be omitted. Similar effects to the first embodiment are also obtained with the second embodiment.

The heat insulation member 209 is housed in the casing 108. The heat insulation member 209 includes a portion located between the electrical component 111 and the like and the sensor unit 104. The heat insulation member 209 suppresses transfer of heat produced by the electrical component 111 and the like to the sensor unit 104. The heat insulation member 209 may be formed from the same material as the heat insulation member 109.

The inside of the casing 108 is divided into a plurality of spaces by the heat insulation member 209, and the sensor unit 104 and the electrical component 111 and the like are located in different spaces to each other. In the second embodiment, the heat insulation member 209 includes an inner side portion between the sensor unit 104 and the base 105. Direct heat transfer from the electrical component 111 and the like to the sensor unit 104 is suppressed by this inner side portion of the heat insulation member 209. An outer side portion of the heat insulation member 209 blocks the space between the upper cover 106 and the base 105. Heat transfer due to convection from the electrical component 111 and the like to the sensor unit 104 is suppressed by the outer side portion of the heat insulation member 209. Also, shock resistance from the side of the casing 108 improves, due to the outer side portion of the heat insulation member 209.

Third Embodiment

Figure 3A:
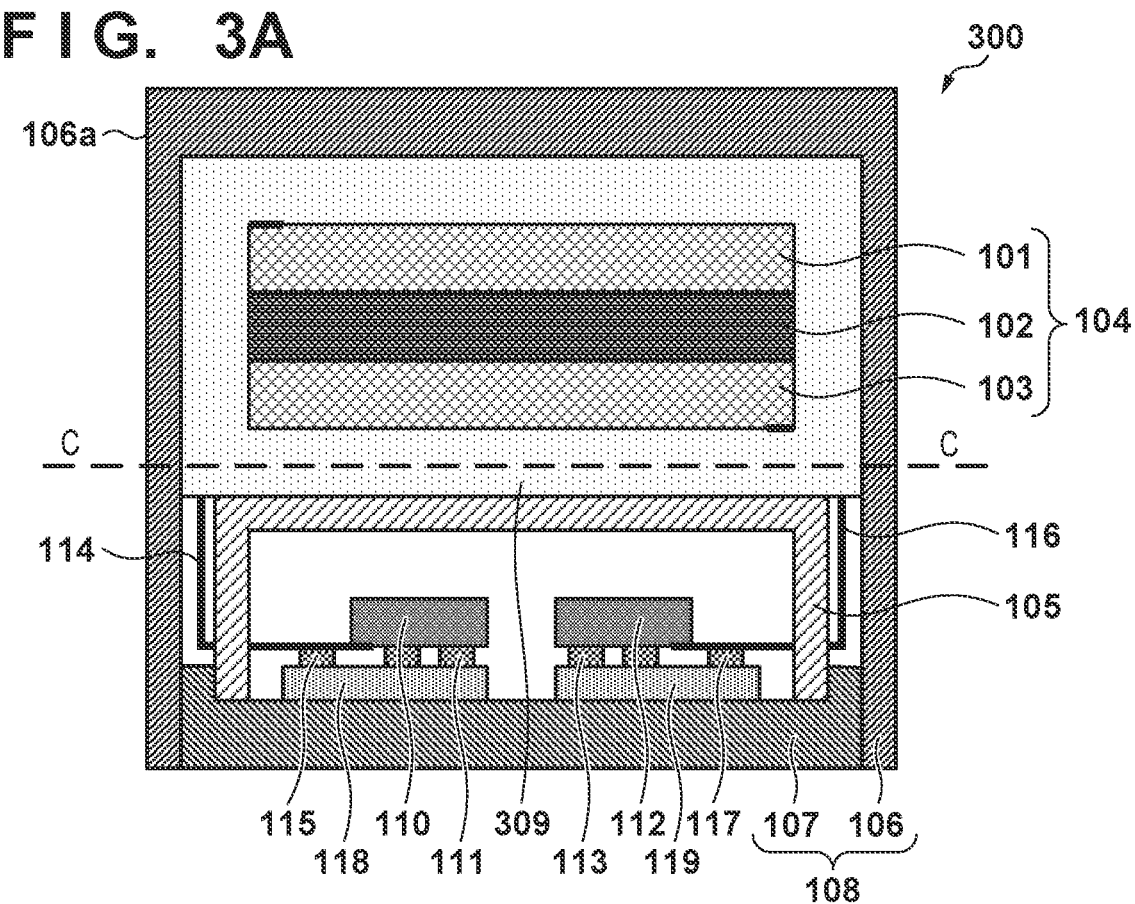
FIGS. 3A and 3B are diagrams illustrating an exemplary configuration of a radiation imaging apparatus of a third embodiment of the present invention.
Figure 3B:
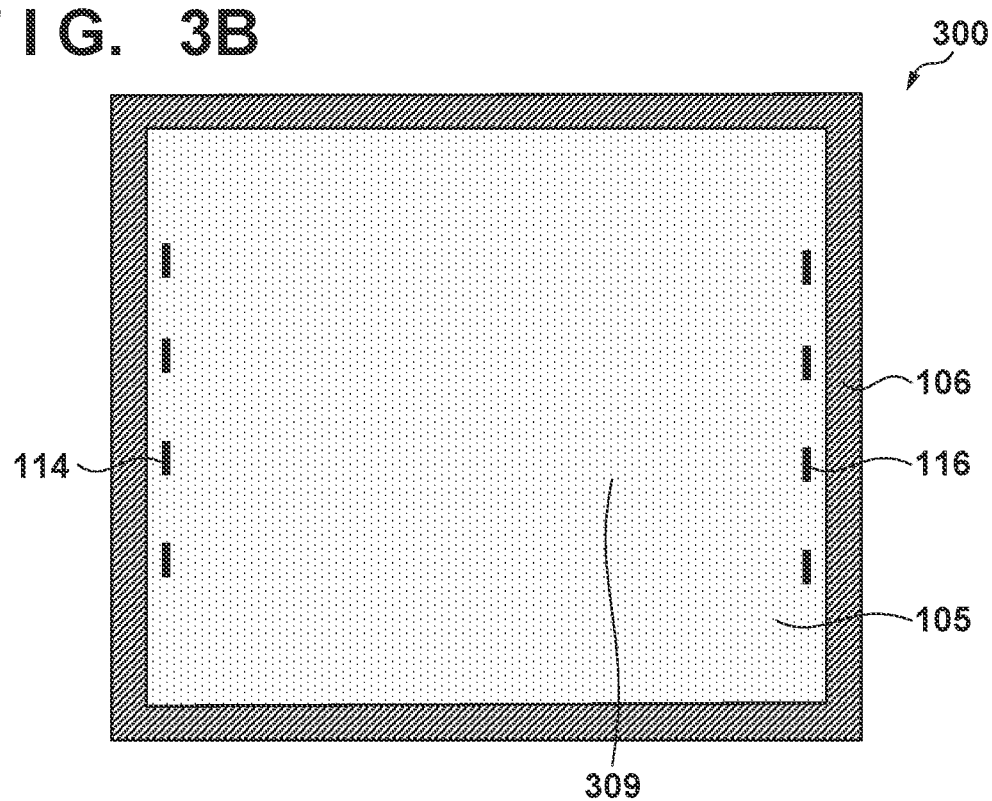

A radiation imaging apparatus 300 according to a third embodiment will be described, with reference to FIGS. 3A and 3B. FIG. 3A shows a cross-sectional view of the radiation imaging apparatus 300 in a plane orthogonal to the incident surface 106a. FIG. 3B shows a cross-sectional view of the radiation imaging apparatus 300 along a C-C line of FIG. 3A. The radiation imaging apparatus 300 differs from the radiation imaging apparatus 100 in terms of having a heat insulation member 309 instead of the heat insulation member 109, and may otherwise be the same. Thus, in the third embodiment, similar description to the first embodiment will be omitted. Similar effects to the first embodiment are also obtained with the third embodiment.

The heat insulation member 309 is housed in the casing 108. The heat insulation member 309 includes a portion located between the electrical component 111 and the like and the sensor unit 104. The heat insulation member 309 suppresses transfer of heat produced by the electrical component 111 and the like to the sensor unit 104. The heat insulation member 309 may be formed from the same material as the heat insulation member 109.

The inside of the casing 108 is divided into a plurality of spaces by the heat insulation member 309, and the sensor unit 104 and the electrical component 111 and the like are located in different spaces to each other. In the third embodiment, the sensor unit 104 is enveloped by the heat insulation member 309. Direct heat transfer from the electrical component 111 and the like to the sensor unit 104 and heat transfer due to convection are suppressed by the heat insulation member 309. Furthermore, because the sensor unit 104 is supported by both the inner surface of the casing 108 and the base 105 due to the heat insulation member 309, shock resistance from the incident surface 106a also improves, in addition to shock resistance from the side of the casing 108.

Fourth Embodiment

Figure 4A:
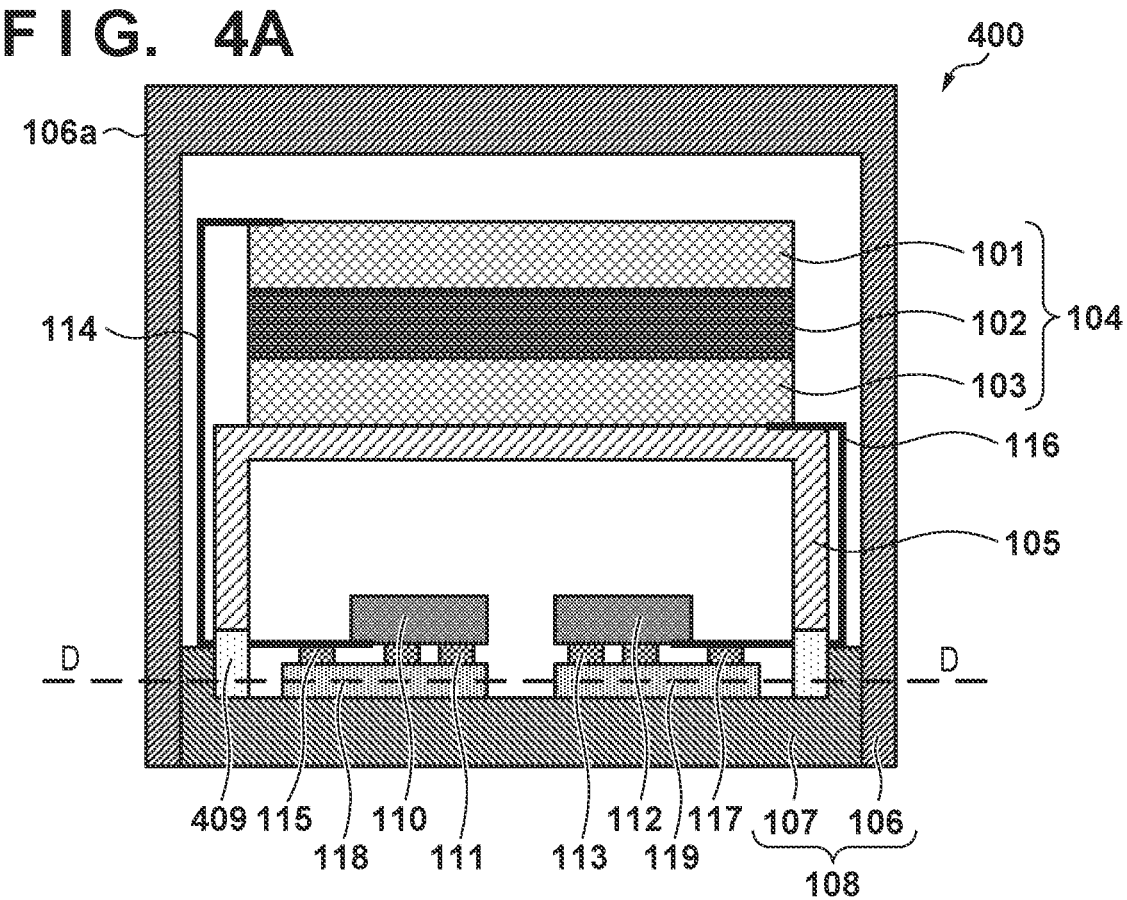
FIGS. 4A and 4B are diagrams illustrating an exemplary configuration of a radiation imaging apparatus of a fourth embodiment of the present invention.
Figure 4B:
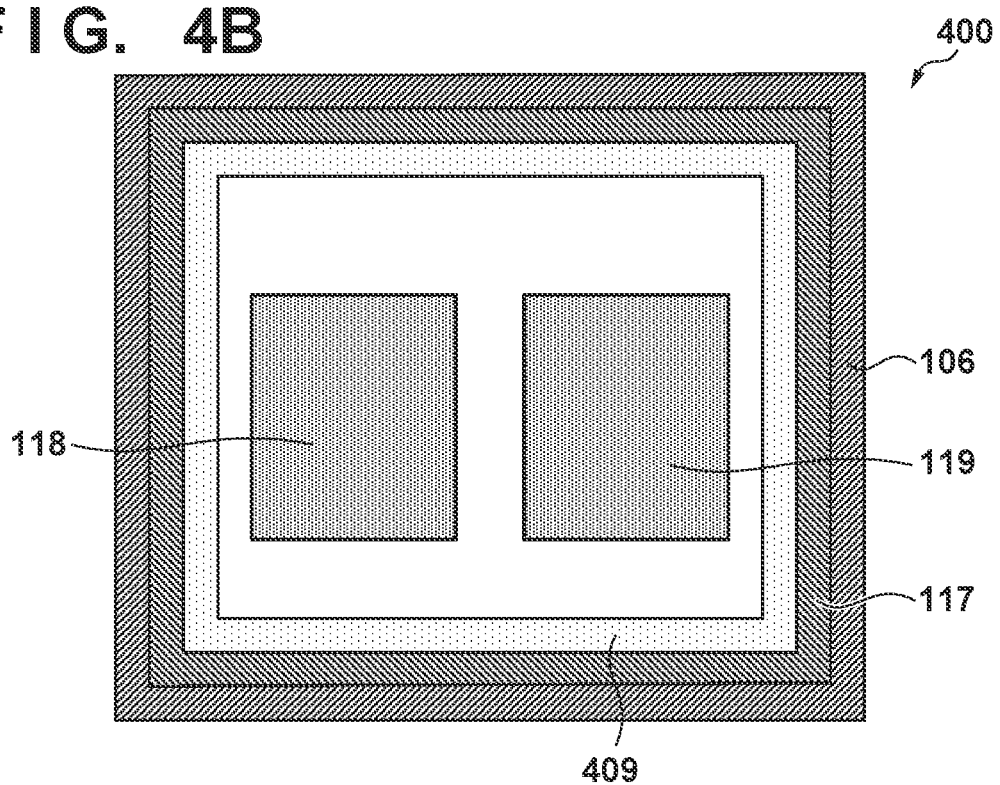

A radiation imaging apparatus 400 according to a fourth embodiment will be described, with reference to FIGS. 4A and 4B. FIG. 4A shows a cross-sectional view of the radiation imaging apparatus 400 in a plane orthogonal to the incident surface 106a. FIG. 4B shows a cross-sectional view of the radiation imaging apparatus 400 along a D-D line of FIG. 4A. The radiation imaging apparatus 400 differs from the radiation imaging apparatus 100 in terms of having a heat insulation member 409 instead of the heat insulation member 109, and may otherwise be the same. Thus, in the fourth embodiment, similar description to the first embodiment will be omitted. Similar effects to the first embodiment are also obtained with the fourth embodiment.

The heat insulation member 409 is housed in the casing 108. The heat insulation member 409 includes a portion sandwiched by the lower cover 107 of the casing 108 and the side walls of the base 105. The heat insulation member 409 may be formed from the same material as the heat insulation member 109. Heat transfer due to convection from the electrical component 111 and the like to the sensor unit 104 is suppressed by the heat insulation member 409.

Embodiment of System

Figure 5:
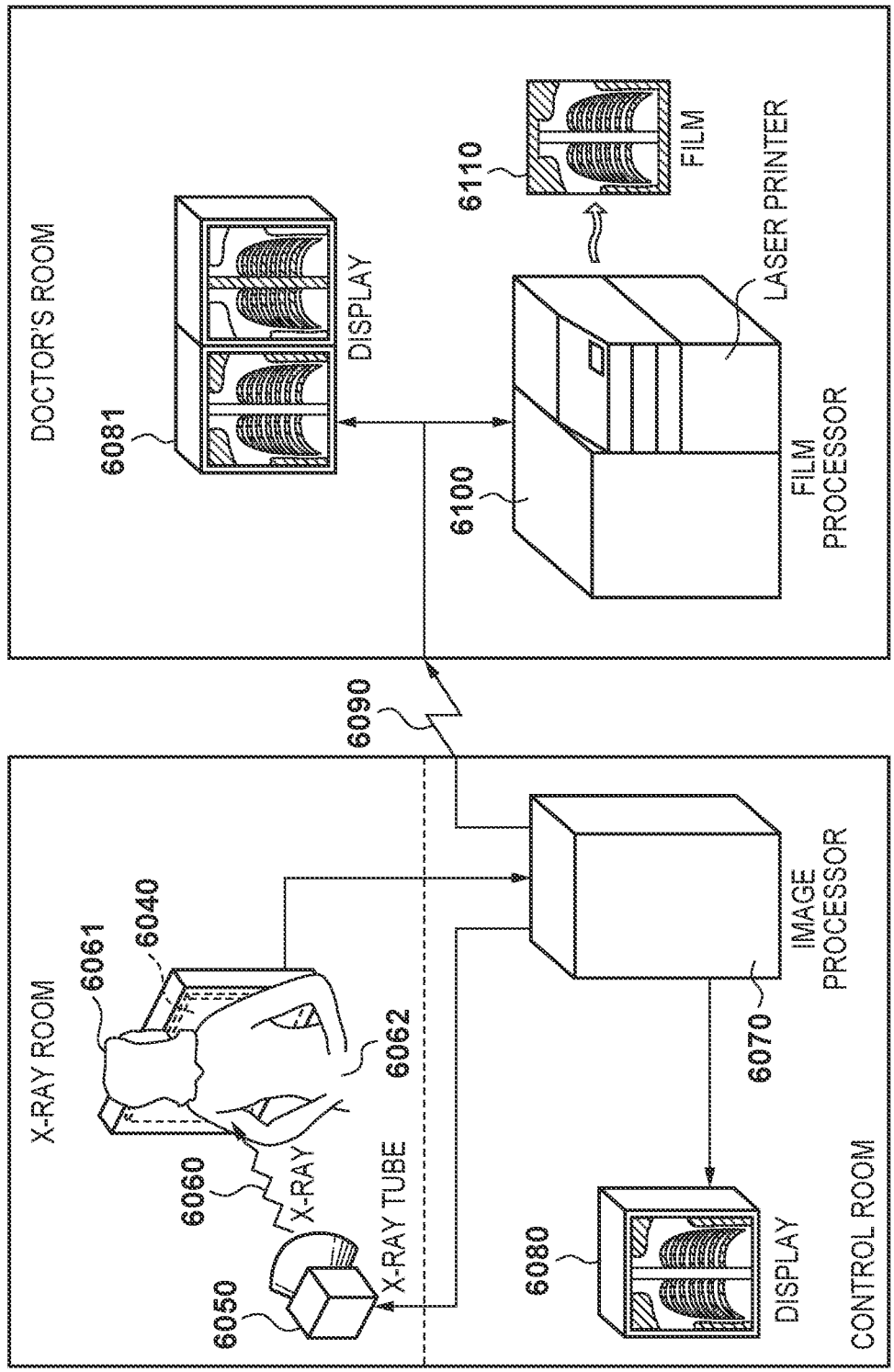
FIG. 5 is a diagram illustrating an exemplary configuration of a radiation imaging system of another embodiment of the present invention.

FIG. 5 is a diagram showing an example of application of a detection apparatus for radiation according to the present invention to an X-ray diagnostic system (radiography system). X-rays 6060 serving as radiation generated by an X-ray tube 6050 (radiation source) pass through a chest 6062 of a subject or a patient 6061, and are incident on one of the abovementioned radiation imaging apparatuses. Information on internal parts of the patient 6061 is included in these incident X-rays. Electrical information is generated in response to incidence of the X-rays. This information is converted into digital signals and image-processed by an image processor 6070 serving as a signal processing unit, and can be observed on a display 6080 serving as a display unit in a control room. Note that the radiation imaging system has at least a radiation imaging apparatus and a signal processing unit that processes signals from the radiation imaging apparatus.

Also, this information can be transferred to a remote location by a transmission processing unit such as a telephone line 6090, and displayed on a display 6081 serving as a display unit in a doctor's office or the like or saved to a recording unit such as an optical disk, thus enabling a doctor in a remote location to make a diagnose. This information can also be recorded on a film 6110 serving as a recording medium by a film processor 6100 serving as a recording unit.

Image quality stability improves due to reducing the difference in how the two sensor boards stacked together are affected by electrical components within the casing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
    a sensor unit including two sensor boards stacked together, each of the two sensor boards being configured to convert incident radiation into an electric signal;
    a base supporting the sensor unit;
    an electrical component on an opposite side of the sensor unit relative to the base; and
    a heat insulation member, wherein
    a portion of the heat insulation member is located between the electrical component and the sensor unit, and
    a heat conductivity of the heat insulation member is lower than a heat conductivity of the base.

2. The radiation imaging apparatus according to claim 1, further comprising a casing housing the sensor unit, the base, the electrical component and the heat insulation member, wherein
    a portion of the heat insulation member blocks a space between the casing and the base.

3. The radiation imaging apparatus according to claim 2, wherein an inside of the casing is divided into a plurality of spaces by the heat insulation member, and
    the sensor unit and the electrical component are located in different spaces from each other.

4. The radiation imaging apparatus according to claim 1, wherein a portion of the heat insulation member opposes the sensor unit relative to the base.

5. The radiation imaging apparatus according to claim 1, wherein a portion of the heat insulation member is located between the sensor unit and the base.

6. The radiation imaging apparatus according to claim 1, wherein the heat insulation member envelops the sensor unit.

7. The radiation imaging apparatus according to claim 1, wherein the sensor unit comprises a filter that reduces radiation of a predetermined wavelength band, said filter being located between the two sensor boards.

8. The radiation imaging apparatus according to claim 1, wherein the heat insulation member comprises rubber or foamed resin.

9. The radiation imaging apparatus according to claim 1, wherein the electrical component includes an integrated circuit configured to control operations of the two sensor boards and/or an integrated circuit configured to process signals from the two sensor boards.

10. A radiation imaging system, comprising:
    the radiation imaging apparatus according to claim 1; and
    a signal processing unit configured to process a signal obtained by the radiation imaging apparatus.

11. The radiation imaging apparatus according to claim 1, further comprising a casing housing the sensor unit, the base, the electrical component and the heat insulation member, wherein
    the heat insulation member contacts the casing.

12. The radiation imaging apparatus according to claim 11, wherein in a planar view of an incident surface of the radiation imaging apparatus, a portion of the heat insulation member is located between the base and the casing.

13. The radiation imaging apparatus according to claim 1, wherein in a planar view of an incident surface of the radiation imaging apparatus, an outer periphery of the insulation member surrounds by an outer periphery of the base.

14. The radiation imaging apparatus according to claim 1, further comprising a cable connecting the sensor unit to the electrical component, wherein
    the cable passes through the insulation member.

15. The radiation imaging apparatus according to claim 14, wherein the cable fits an opening of the insulation member.

16. A radiation imaging apparatus, comprising:
    a sensor unit including two sensor boards stacked together, each of the two sensor boards configured to convert incident radiation into an electric signal;
    a base supporting the sensor unit;
    an electrical component on an opposite side of the sensor unit relative to the base;
    a casing housing the sensor unit, the base and the electrical component; and
    a heat insulation member, wherein
    a portion of the heat insulation member blocks a space between the casing and the base, and
    a heat conductivity of the heat insulation member is lower than a heat conductivity of the base.

17. The radiation imaging apparatus according to claim 16, wherein the base has a box-like shape with an opening that is open on an opposite side to the sensor unit, and
    a portion of the heat insulation member is sandwiched by the casing and side walls of the base.

* * * * *